United States Patent
Peters et al.

(10) Patent No.: US 7,378,526 B2
(45) Date of Patent: May 27, 2008

(54) AZACYCLIC ETHYNYL DERIVATIVES

(75) Inventors: Dan Peters, Ballerup (DK); Gunnar M. Olsen, Ballerup (DK); Elsebet Østergaard Nielsen, Ballerup (DK); Tino Dyhring Jørgensen, Ballerup (DK); Philip K. Ahring, Ballerup (DK)

(73) Assignee: Neurosearch A/S, Ballerup (DK)

( * ) Notice: Subject to any disclaimer, the term of this patent is extended or adjusted under 35 U.S.C. 154(b) by 512 days.

(21) Appl. No.: 10/513,416

(22) PCT Filed: May 6, 2003

(86) PCT No.: PCT/DK03/00294

§ 371 (c)(1),
(2), (4) Date: Nov. 4, 2004

(87) PCT Pub. No.: WO03/094830

PCT Pub. Date: Nov. 20, 2003

(65) Prior Publication Data

US 2005/0171078 A1     Aug. 4, 2005

(30) Foreign Application Priority Data

May 7, 2002    (DK) .............................. 2002 00691

(51) Int. Cl.
*C07D 401/00* (2006.01)
*C07D 451/02* (2006.01)
*C07D 405/00* (2006.01)

(52) U.S. Cl. ...................... 546/200; 546/124; 546/125; 546/126

(58) Field of Classification Search ................ 546/124, 546/125, 126, 200
See application file for complete search history.

(56) References Cited

U.S. PATENT DOCUMENTS 6,624,167 B1    9/2003    Clark et al.

2003/0119880 A1    6/2003    Kim et al.

FOREIGN PATENT DOCUMENTS

| WO | WO-96/36609 A1 | 11/1996 |
|---|---|---|
| WO | WO-97/13770 A1 | 4/1997 |
| WO | WO 98/54181 A1 | 12/1998 |
| WO | WO-00/32600 A1 | 6/2000 |
| WO | WO-01-16121 A1 | 3/2001 |
| WO | WO 01/16121 A1 * | 8/2001 |
| WO | WO-02/08205 A1 | 1/2002 |
| WO | WO-02/30405 A2 | 4/2002 |
| WO | WO-03/033495 A1 | 4/2003 |
| WO | WO-03028650 A2 | 4/2003 |

OTHER PUBLICATIONS

Koh et al. Journal of Organic Chemistry, 1996, 61(14), 4494-4495.*
Libman, N. M. et al., Aminoalcohols of the acetylene series. IX. 3,3-Diphenyl-3hydroxpropinyl quinuclidines: XP002263120 abstract & Khimiko-Farmatzevticheskii Zhurnal (1986), 20(11), 1308-12. Document No. 106:95586.
Brown et al., J. Med. Chem. 1999, 42, 1306-1311.

* cited by examiner

*Primary Examiner*—D. Margaret Seaman
*Assistant Examiner*—Nizal S. Chandrakumar
(74) *Attorney, Agent, or Firm*—Birch, Stewart, Kolasch & Birch, LLP

(57) ABSTRACT

This invention relates to novel azacyclic ethynyl derivatives, which are found to be cholinergic ligands at the nicotinic acetylcholine receptors and modulators of the monoamine receptors and transporters.

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

4 Claims, No Drawings

AZACYCLIC ETHYNYL DERIVATIVES

TECHNICAL FIELD

This invention relates to novel azacyclic ethynyl derivatives, which are found to be cholinergic ligands at the nicotinic acetylcholine receptors and modulators of the monoamine receptors and transporters.

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

BACKGROUND ART

The endogenous cholinergic neurotransmitter, acetylcholine, exert its biological effect via two types of cholinergic receptors, the muscarinic Acetyl Choline Receptors (mAChR) and the nicotinic Acetyl Choline Receptors (nAChR).

As it is well established that muscarinic acetylcholine receptors dominate quantitatively over nicotinic acetylcholine receptors in the brain area important to memory and cognition, and much research aimed at the development of agents for the treatment of memory related disorders have focused on the synthesis of muscarinic acetylcholine receptor modulators.

Recently, however, an interest in the development of nAChR modulators has emerged. Several diseases are associated with degeneration of the cholinergic system i.e. senile dementia of the Alzheimer type, vascular dementia and cognitive impairment due to the organic brain damage disease related directly to alcoholism. Indeed several CNS disorders can be attributed to a cholinergic deficiency, a dopaminergic deficiency, an adrenergic deficiency or a serotonergic deficiency.

WO 200208205 (Krenitsky Pharmaceuticals) describes substituted 4-alkynyl pyrimidinyl derivatives having NGF-like activity. However, the un-substituted and N-substituted azacyclic ethynyl derivatives of the present invention are not disclosed.

SUMMARY OF THE INVENTION

The present invention is devoted to the provision novel modulators of the nicotinic and/or of the monoamine receptors, which modulators are useful for the treatment of diseases or disorders related to the cholinergic receptors, and in particular the nicotinic acetylcholine receptor (nAChR), the serotonin receptor (5-HTR), the dopamine receptor (DAR) and the norepinephrine receptor (NER), and of the biogenic amine transporters for serotonin (5-HT), dopamine (DA) and norepinephrine (NE).

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

The compounds of the invention may also be useful as diagnostic tools or monitoring agents in various diagnostic methods, and in particular for in vivo receptor imaging (neuroimaging), and they may be used in labelled or unlabelled form.

In its first aspect the invention provides novel azacyclic ethynyl derivatives represented by Formula I:

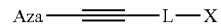

any of its enantiomers or any mixture of its enantiomers, or a pharmaceutically acceptable salt thereof, wherein Aza represents an azacyclic or azabicyclic group, which azacyclic or azabicyclic group is optionally N-substituted with alkyl, cycloalkyl, cycloalkylalkyl, aryl or aralkyl, and which N-substituted azacyclic group may in particular be an aza-onium salt;

L may be absent or present, and if present represents a linking group selected from $-CH_2-$, $-CH_2-CH_2-$, $-CH_2-CH_2-CH_2-$, $-CH=CH-$, $-CH_2-CH=CH-$, $-CH=CH-CH_2-$, $-C\equiv C-$, $-CH_2-C\equiv C-$, and $-C\equiv C-CH_2-$; and X represents Ar, Alk or cAlk, wherein Ar represents an aromatic mono- or polycyclic, carbocyclic or heterocyclic group, which aromatic cyclic group is optionally substituted one or more times with alkyl, cycloalkyl, cycloalkylalkyl, alkoxy, cycloalkoxy, halogen, $CF_3$, $OCF_3$, cyano, amino, nitro, aryl, aryloxy and/or aralkyl;

Alk represents an alkenyl or alkynyl group, which alkenyl and alkynyl groups may be straight or branched, and which alkenyl and alkynyl groups are optionally substituted one or more times with alkyl, cycloalkyl, cycloalkylalkyl, alkoxy, cycloalkoxy, halogen, $CF_3$, $OCF_3$, cyano, amino, nitro, aryl, aryloxy and/or aralkyl; and cAlk represents a cyclic alkenyl or alkynyl group, which cyclic alkenyl and alkynyl group are optionally substituted one or more times with alkyl, cycloalkyl, cycloalkylalkyl, alkoxy, cycloalkoxy, halogen, $CF_3$, $OCF_3$, cyano, amino, nitro, aryl, aryloxy and/or aralkyl.

In its second aspect the invention provides pharmaceutical compositions comprising a therapeutically effective amount of the azacyclic ethynyl derivative of the invention, or a pharmaceutically-acceptable addition salt thereof, together with at least one pharmaceutically-acceptable carrier or diluent.

In a further aspect the invention relates to the use of the azacyclic ethynyl derivative of the invention, or a pharmaceutically-acceptable addition salt thereof, for the manufacture of a pharmaceutical composition/medicament for the treatment, prevention or alleviation of a disease or a disorder or a condition of a mammal, including a human, which disease, disorder or condition is responsive to modulation of cholinergic receptors and/or monoamine receptors.

In a final aspect the invention provides methods of treatment, prevention or alleviation of diseases, disorders or conditions of a living animal body, including a human, which disorder, disease or condition is responsive to modulation of cholinergic receptors and/or monoamine receptors, which method comprises the step of administering to such a living animal body in need thereof a therapeutically effective amount of the azacyclic ethynyl derivative of the invention.

Other objects of the invention will be apparent to the person skilled in the art from the following detailed description and examples.

DETAILED DISCLOSURE OF THE INVENTION

Azacyclic Ethynyl Derivative

In a first aspect novel azacyclic ethynyl derivatives are provided. The azacyclic ethynyl derivatives of the invention may be represented by the general Formula I:

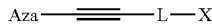

any of its enantiomers or any mixture of its enantiomers, or a pharmaceutically acceptable salt thereof, wherein Aza represents an azacyclic or azabicyclic group, which azacyclic or azabicyclic group is optionally N-substituted with alkyl, cycloalkyl, cycloalkylalkyl, aryl or aralkyl, and which N-substituted azacyclic group may in particular be an aza-onium salt;

L may be absent (i.e. represent a single-covalent-bond) or present, and if present represents a linking group selected from —$CH_2$—, —$CH_2$—$CH_2$—, —$CH_2$—$CH_2$—$CH_2$—, —CH=CH—, —$CH_2$—CH=CH—, —CH=CH—$CH_2$—, —C≡C—, —$CH_2$—C≡C—, and —C≡C—$CH_2$—; and X represents Ar, Alk or cAlk; wherein Ar represents an aromatic mono- or polycyclic, carbocyclic or heterocyclic group, which aromatic cyclic group is optionally substituted one or more times with alkyl, cycloalkyl, cycloalkylalkyl, alkoxy, cycloalkoxy, halogen, $CF_3$, $OCF_3$, cyano, amino, nitro, aryl, aryloxy and/or aralkyl;

Alk represents an alkenyl or alkynyl group, which alkenyl and alkynyl groups may be straight or branched, and which alkenyl and alkynyl groups are optionally substituted one or more times with alkyl, cycloalkyl, cycloalkylalkyl, alkoxy, cycloalkoxy, halogen, $CF_3$, $OCF_3$, cyano, amino, nitro, aryl, aryloxy and/or aralkyl; and cAlk represents a cyclic alkenyl or alkynyl group, which cyclic alkenyl and alkynyl group are optionally substituted one or more times with alkyl, cycloalkyl, cycloalkylalkyl, alkoxy, cycloalkoxy, halogen, $CF_3$, $OCF_3$, cyano, amino, nitro, aryl, aryloxy and/or aralkyl.

In a $1^{st}$ preferred embodiment Aza represents an azacyclic or azabicyclic group, which is optionally N-substituted with alkyl, cycloalkyl, cycloalkylalkyl, aryl or aralkyl, and may in particular be an aza-onium salt.

In a $2^{nd}$ preferred embodiment the azacyclic group is selected from the group consisting of Aza I to Aza IX, presented below:

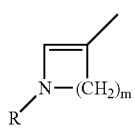
(Aza I)

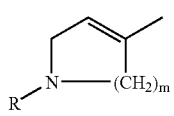
(Aza II)

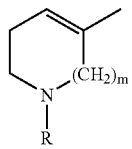
(Aza III)

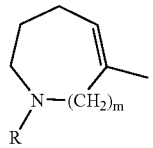
(Aza IV)

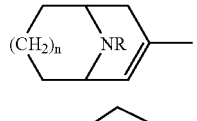
(Aza V)

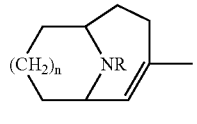
(Aza VI)

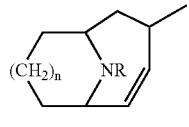
(Aza VII)

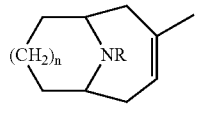
(Aza VIII)

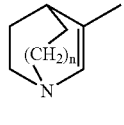
(Aza IX)

- - - - - represents a single bond or an optional double bond;

m is 1, 2 or 3;

n is 0, 1, 2 or 3; and

R represents hydrogen, alkyl, cycloalkyl, cycloalkylalkyl, aryl or aralkyl;

or an aza-onium salt thereof.

In a $3^{rd}$ preferred embodiment L is present and represents a linking group selected from —$CH_2$—, —$CH_2$—$CH_2$—, —CH=CH— and —C≡C—.

In a $4^{th}$ preferred embodiment the azacyclic ethynyl derivative of the invention is represented by Formula I, wherein X is Ar, and Ar represents an aryl group, which aryl group is optionally substituted one or more times with substituents selected from alkyl, cycloalkyl, cycloalkylalkyl, alkoxy, cycloalkoxy, halogen, $CF_3$, $OCF_3$, cyano, amino, nitro, aryl, aryloxy and/or aralkyl.

In a more preferred embodiment Ar represents an aryl group selected from phenyl, indenyl, naphthyl, azulenyl, fluorenyl, and anthracenyl, which aryl group is optionally substituted one or more times with substituents selected from alkyl, cycloalkyl, cycloalkylalkyl, alkoxy, cycloalkoxy, halogen, $CF_3$, $OCF_3$, cyano, amino, nitro, aryl, aryloxy and/or aralkyl.

In an even more preferred embodiment Ar is phenyl, which phenyl group is optionally substituted one or more times with substituents selected from alkyl, cycloalkyl, cycloalkylalkyl, alkoxy, cycloalkoxy, halogen, $CF_3$, $OCF_3$, cyano, amino and/or nitro.

In a 5$^{th}$ preferred embodiment the azacyclic ethynyl derivative of the invention is represented by Formula I, wherein X is Ar, and Ar represents an aromatic 5- or 6-membered monocyclic heterocyclic group, which monocyclic heterocyclic group is optionally substituted one or more times with alkyl, cycloalkyl, cycloalkylalkyl, alkoxy, cycloalkoxy, halogen, $CF_3$, $OCF_3$, cyano, amino, nitro, aryl, aryloxy and/or aralkyl.

In a more preferred embodiment the aromatic 5- or 6-membered monocyclic heterocyclic group is furanyl, in particular 2- or 3-furanyl; thienyl, in particular 2 or 3-thienyl; pyrrolyl (azolyl), in particular 1,2 or 3-pyrrolyl; oxazolyl, in particular oxazol-2,4 or 5-yl; thiazolyl, in particular thiazol-2,4 or 5-yl; imidazolyl, in particular 1,2 or 4-imidazolyl; pyrazolyl, in particular 1,3 or 4-pyrazolyl; isoxazolyl, in particular isoxazol-3,4 or 5-yl; isothiazolyl, in particular isothiazol-3,4 or 5-yl; oxadiazolyl, in particular 1,2,3-, 1,2,4-, 1,2,5- or 1,3,4-oxadiazol-3,4 or 5-yl; triazolyl, in particular 1,2,3-, 1,2,4-, 2,1,3- or 4,1,2-triazolyl; thiadiazolyl, in particular thiadiazol-3,4 or 5-yl; pyridinyl, in particular 2,3 or 4-pyridinyl; pyridazinyl, in particular 3 or 4-pyridazinyl; pyrimidinyl, in particular 2,4 or 5-pyrimidinyl; pyrazinyl, in particular 2 or 3-pyrazinyl; or triazinyl, in particular 1,2,3-, 1,2,4- or 1,3,5-triazinyl.

In a 6$^{th}$ preferred embodiment the azacyclic ethynyl derivative of the invention is represented by Formula I, wherein X is Ar, and Ar represents an aromatic bicyclic heterocyclic group, which bicyclic heterocyclic group is optionally substituted one or more times with alkyl, cycloalkyl, cycloalkylalkyl, alkoxy, cycloalkoxy, halogen, $CF_3$, $OCF_3$, cyano, amino, nitro, aryl, aryloxy and/or aralkyl.

In a more preferred embodiment the bicyclic heterocyclic group is indolizinyl, in particular 2,5 or 6-indolizinyl; indolyl, in particular 2,5 or 6-indolyl; isoindolyl, in particular 2,5 or 6-isoindolyl; benzo[b]furanyl, in particular 2,5 or 6-benzofuranyl; benzo[b]thienyl, in particular 2,5 or 6-benzothienyl; benzimidazolyl, in particular 2,5 or 6-benzimidazolyl; benzothiazolyl, in particular 5 or 6-benzothiazolyl; purinyl, in particular 2 or 8-purinyl; quinolinyl, in particular 2,3,6 or 7-quinolinyl; isoquinolinyl, in particular 3,6 or 7-isoquinolinyl; cinnolinyl, in particular 6 or 7-cinnolinyl; phthalazinyl, in particular 6 or 7-phthalazinyl; quinazolinyl, in particular 2,6 or 7-quinazolinyl; quinoxalinyl, in particular 2 or 6-quinoxalinyl; 1,8-naphthyridinyl, in particular 1,8-naphthyridin-2,3,6 or 7-yl; or pteridinyl, in particular 2,6 or 7-pteridinyl.

In a 7$^{th}$ preferred embodiment the azacyclic ethynyl derivative of the invention is represented by Formula I, wherein X is Alk, and Alk represents an alkenyl or alkynyl group, which alkenyl and alkynyl groups may be straight or branched, and which alkenyl and alkynyl groups are optionally substituted one or more times with alkyl, cycloalkyl, cycloalkylalkyl, alkoxy, cycloalkoxy, halogen, $CF_3$, $OCF_3$, cyano, amino, nitro, aryl, aryloxy and/or aralkyl.

In a more preferred embodiment Alk represents an ethenyl group; a 1- or 2-propenyl (allyl) group; a straight or branched 1-, 2- or 3-butenyl, or 1,3-butdienyl group; a straight or branched 1-, 2-, 3-, 4- or 5-hexenyl, or 1,3-hexdienyl, or 1,3,5-hextrienyl group; a straight or branched 1-, 2-, 3-, 4-, 5-, 6-, or 7-octenyl, or 1,3-octdienyl, or 1,3,5-octtrienyl, or 1,3,5,7-octtetraenyl group; or an ethynyl group; a 1-, or 2-propynyl group; a straight or branched 1-, 2-, or 3-butynyl, or 1,3-butdiynyl group; a straight or branched 1-, 2-, 3-, 4-pentynyl, or 1,3-pentdiynyl group; a straight or branched 1-, 2-, 3-, 4-, or 5-henynyl, or 1,3-hexdiynyl or 1,3,5-hextriynyl group; a straight or branched 1-, 2-, 3-, 4-, 5- or 6-heptynyl, or 1,3-heptdiynyl, or 1,3,5-hepttriynyl group; a straight or branched 1-, 2-, 3-, 4,5-, 6- or 7-octynyl, or 1,3-octdiynyl, or 1,3,5-octtriynyl, or 1,3,5,7-octtetraynyl group.

In an 8$^{th}$ preferred embodiment the azacyclic ethynyl derivative of the invention is represented by Formula I, wherein R is cAlk, and cAlk represents a cyclic alkenyl or alkynyl group, which cyclic alkenyl and alkynyl group are optionally substituted one or more times with alkyl, cycloalkyl, cycloalkylalkyl, alkoxy, cycloalkoxy, halogen, $CF_3$, $OCF_3$, cyano, amino, nitro, aryl, aryloxy and/or aralkyl.

In a more preferred embodiment cAlk represents a cyclopent-1-enyl group; a cyclopenta-1,3-dienyl group; a cyclohex-1-enyl group; a cyclohexa-1,3-dienyl group; a cyclohept-1-enyl group; a cyclohepta-1,3-dienyl group; a cyclooct-1-enyl group; or a cycloocta-1,3-dienyl group.

In a 9$^{th}$ preferred embodiment the azacyclic ethynyl derivative of the invention is represented by Formula I, wherein

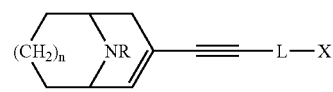

represents a double bond.

In a 10$^{th}$ preferred embodiment the azacyclic ethynyl derivative of the invention is represented by Formula II:

wherein n is 0, 1 or 2;

R represents hydrogen, alkyl or cycloalkyl;

L may be absent or present, and if present represents a linking group selected from —$CH_2$—, —$CH_2$—$CH_2$—, —$CH_2$—$CH_2$—$CH_2$—, —CH=CH—, —$CH_2$—CH=CH—, —CH=CH—$CH_2$—, —C≡C—, —$CH_2$—C≡C— and —C≡C—$CH_2$—; and X represents Ar, Alk or cAlk, wherein Ar represents an aromatic mono- or polycyclic, carbocyclic or heterocyclic group, which aromatic cyclic group is optionally substituted one or more times with alkyl, cycloalkyl, cycloalkylalkyl, alkoxy, cycloalkoxy, halogen, $CF_3$, $OCF_3$, cyano, amino, nitro, aryl, aryloxy and/or aralkyl;

Alk represents an alkenyl or alkynyl group, which alkenyl and alkynyl groups may be straight or branched, and which alkenyl and alkynyl groups are optionally substituted one or more times with alkyl, cycloalkyl, cycloalkylalkyl, alkoxy, cycloalkoxy, halogen, $CF_3$, $OCF_3$, cyano, amino, nitro, aryl, aryloxy and/or aralkyl; and cAlk represents a cyclic alkenyl or alkynyl group, which cyclic alkenyl and alkynyl group are optionally substituted one or more times with alkyl, cycloalkyl, cycloalkylalkyl, alkoxy, cycloalkoxy, halogen, $CF_3$, $OCF_3$, cyano, amino, nitro, aryl, aryloxy and/or aralkyl.

In a more preferred embodiment the azacyclic ethynyl derivative of the invention is represented by Formula II, wherein n is 0 or 1;
R represents hydrogen or alkyl;
L is absent;
X represents a phenyl group, which phenyl is optionally substituted one or two times with alkyl, cycloalkyl, alkoxy, cycloalkoxy, halogen, $CF_3$, $OCF_3$, cyano, amino, or nitro; or an ethenyl group; a 1- or 2-propenyl (allyl) group; a straight or branched 1-, 2- or 3-butenyl, or 1,3-butdienyl group; or a cyclohex-1-enyl group; a cyclohexa-1,3-dienyl group; a cyclohept-1-enyl group; or a cyclohepta-1,3-dienyl group.

In a most preferred embodiment the azacyclic ethynyl derivative of the invention is (±)-8-Methyl-3-phenyletynyl-8-azabicyclo[3.2.1]oct-2-ene;
(±)-8,8-Dimethyl-3-phenyletynyl-8-azabicyclo[3.2.1]oct-2-ene iodide;
(±)-8-H-3-Phenyletynyl-8-azabicyclo[3.2.1]oct-2-ene;
(±)-8-Methyl-3-(2,4-difluorophenyletynyl)-8-azabicyclo[3.2.1]oct-2-ene;
(±)-8-Methyl-3-(1-cyclohexenyletynyl)-8-azabicyclo[3.2.1]oct-2-ene;
(±)-8-Methyl-3-(4-toluyletynyl)-8-azabicyclo[3.2.1]oct-2-ene;
(±)-8-Methyl-3-(4-methoxyphenyletynyl)-8-azabicyclo[3.2.1]oct-2-ene; or
(±)-8-Methyl-3-(2-methyl-but-1-en-3-ynyl)-8-azabicyclo[3.2.1]oct-2-ene;

or an enantiomer or a mixture of its enantiomers, or a pharmaceutically acceptable salt thereof, or an aza-onium salt thereof.

In another preferred embodiment the azacyclic ethynyl derivative of the invention is represented by Formula II, wherein n is 0 or 1;
R represents hydrogen or alkyl;
L represents —$CH_2$—, —CH=CH—, or —C≡C—;
X represents a phenyl group, which phenyl is optionally substituted one or two times with alkyl, cycloalkyl, alkoxy, cycloalkoxy, halogen, $CF_3$, $OCF_3$, cyano, amino, or nitro; or an ethenyl group; a 1- or 2-propenyl (allyl) group; a straight or branched 1-, 2- or 3-butenyl, or 1,3-butdienyl group; or a cyclohex-1-enyl group; a cyclohexa-1,3-dienyl group; a cyclohept-1-enyl group; or a cyclohepta-1,3-dienyl group.

In a most preferred embodiment the azacyclic ethynyl derivative of the invention is (±)-8-Methyl-3-phenylbuta-1,3-diynyl-8-azabicyclo[3.2.1]oct-2-ene; or
(±)-8-Methyl-3-(3-phenylpropyn-1-yl)-8-azabicyclo[3.2.1]oct-2-ene;

or an enantiomer or a mixture of its enantiomers, or a pharmaceutically acceptable salt thereof, or an aza-onium salt thereof.

In an 11$^{th}$ preferred embodiment the azacyclic ethynyl derivative of the invention is represented by Formula III:

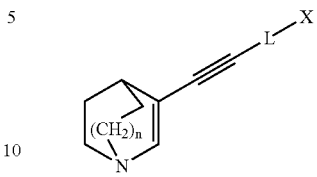

wherein n is 0 or 1;

L may be absent or present, and if present represents a linking group selected from —$CH_2$—, —$CH_2$—$CH_2$—, —$CH_2$—$CH_2$—$CH_2$—, —CH=CH—, —$CH_2$—CH=CH—, —CH=CH—$CH_2$—, —C≡C—, —$CH_2$—C≡C—, and —C≡C—$CH_2$—; and X represents Ar, Alk or cAlk, wherein Ar represents an aromatic mono- or polycyclic, carbocyclic or heterocyclic group, which aromatic cyclic group is optionally substituted one or more times with alkyl, cycloalkyl, cycloalkylalkyl, alkoxy, cycloalkoxy, halogen, $CF_3$, $OCF_3$, cyano, amino, nitro, aryl, aryloxy and/or aralkyl;

Alk represents an alkenyl or alkynyl group, which alkenyl and alkynyl groups may be straight or branched, and which alkenyl and alkynyl groups are optionally substituted one or more times with alkyl, cycloalkyl, cycloalkylalkyl, alkoxy, cycloalkoxy, halogen, $CF_3$, $OCF_3$, cyano, amino, nitro, aryl, aryloxy and/or aralkyl; and cAlk represents a cyclic alkenyl or alkynyl group, which cyclic alkenyl and alkynyl group are optionally substituted one or more times with alkyl, cycloalkyl, cycloalkylalkyl, alkoxy, cycloalkoxy, halogen, $CF_3$, $OCF_3$, cyano, amino, nitro, aryl, aryloxy and/or aralkyl.

In a more preferred embodiment the azacyclic ethynyl derivative of the invention is represented by Formula III, wherein n is 0 or 1;
L is absent;
X represents a phenyl group, which phenyl is optionally substituted one or two times with alkyl, cycloalkyl, alkoxy, cycloalkoxy, halogen, $CF_3$, $OCF_3$, cyano, amino, or nitro; or an ethenyl group; a 1- or 2-propenyl (allyl) group; a straight or branched 1-, 2- or 3-butenyl, or 1,3-butdienyl group; or a cyclohex-1-enyl group; a cyclohexa-1,3-dienyl group; a cyclohept-1-enyl group; or a cyclohepta-1,3-dienyl group.

In a most preferred embodiment the azacyclic ethynyl derivative of the invention is (±)-3-Phenyletynyl-quinuclidin-2-ene;
(±)-1-Methyl-3-phenyletynyl-quinuclidin-2-ene; or
(±)-3-(1-Cyclohexenyletynyl)-quinuclidine-2-ene;

or an enantiomer or a mixture of its enantiomers, or a pharmaceutically acceptable salt thereof, or an aza-onium salt thereof.

In a 12$^{th}$ preferred embodiment the azacyclic ethynyl derivative of the invention is represented by Formula IV:

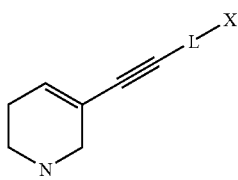

wherein

L may be absent or present, and if present represents a linking group selected from —CH$_2$—, —CH$_2$—CH$_2$—, —CH$_2$—CH$_2$—CH$_2$—, —CH=CH—, —CH$_2$—CH=CH—, —CH=CH—CH$_2$—, —C≡C—, —CH$_2$—C≡C—, and —C≡C—CH$_2$—; and X represents Ar, Alk or cAlk, wherein Ar represents an aromatic mono- or polycyclic, carbocyclic or heterocyclic group, which aromatic cyclic group is optionally substituted one or more times with alkyl, cycloalkyl, cycloalkylalkyl, alkoxy, cycloalkoxy, halogen, CF$_3$, OCF$_3$, cyano, amino, nitro, aryl, aryloxy and/or aralkyl;

Alk represents an alkenyl or alkynyl group, which alkenyl and alkynyl groups may be straight or branched, and which alkenyl and alkynyl groups are optionally substituted one or more times with alkyl, cycloalkyl, cycloalkylalkyl, alkoxy, cycloalkoxy, halogen, CF$_3$, OCF$_3$, cyano, amino, nitro, aryl, aryloxy and/or aralkyl; and cAlk represents a cyclic alkenyl or alkynyl group, which cyclic alkenyl and alkynyl group are optionally substituted one or more times with alkyl, cycloalkyl, cycloalkylalkyl, alkoxy, cycloalkoxy, halogen, CF$_3$, OCF$_3$, cyano, amino, nitro, aryl, aryloxy and/or aralkyl.

In a more preferred embodiment the azacyclic ethynyl derivative of the invention is represented by Formula IV, wherein L is absent;

X represents a phenyl group, which phenyl is optionally substituted one or two times with alkyl, cycloalkyl, alkoxy, cycloalkoxy, halogen, CF$_3$, OCF$_3$, cyano, amino, or nitro; or an ethenyl group; a 1- or 2-propenyl (allyl) group; a straight or branched 1-, 2- or 3-butenyl, or 1,3-butdienyl group; or a cyclohex-1-enyl group; a cyclohexa-1,3-dienyl group; a cyclohept-1-enyl group; or a cyclohepta-1,3-dienyl group.

In a most preferred embodiment the azacyclic ethynyl derivative of the invention is
3-Phenyletynyl-1,2,5,6-tetrahydropyridine; or
N-Methyl-3-phenyletynyl-1,2,5,6-tetrahydropyridine;

or an enantiomer or a mixture of its enantiomers, or a pharmaceutically acceptable salt thereof, or an aza-onium salt thereof.

Definition of Substituents

In the context of this invention halo represents a fluorine, a chlorine, a bromine or an iodine atom.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an alkoxy group designates an "alkyl-O—" group, wherein alkyl is as defined above. Examples of preferred alkoxy groups of the invention include methoxy and ethoxy.

In the context of this invention an alkenyl group designates a straight or branched carbon chain containing one or more double bonds, including di-enes, tri-ene and poly-enes. In a preferred embodiment the alkenyl group of the invention comprises of from two to eight carbon atoms ($C_{2-8}$-alkenyl), more preferred of from two to six carbon atoms ($C_{2-6}$-alkenyl), including at least one double bond. In a most preferred embodiment the alkenyl group of the invention is ethenyl; 1- or 2-propenyl (allyl); 1-, 2- or 3-butenyl, or 1,3-butdienyl; 1-, 2-, 3-, 4- or 5-hexenyl, or 1,3-hexdienyl, or 1,3,5-hextrienyl; 1-, 2-, 3-, 4-, 5-, 6-, or 7-octenyl, or 1,3-octdienyl, or 1,3,5-octtrienyl, or 1,3,5,7-octtetraenyl.

In the context of this invention an alkynyl group designates a straight or branched carbon chain containing one or more triple bonds, including di-ynes, tri-ynes and poly-ynes. In a preferred embodiment the alkynyl group of the invention comprises of from two to eight carbon atoms ($C_{2-8}$-alkynyl), more preferred of from two to six carbon atoms ($C_{2-6}$-alkynyl), including at least one triple bond. In its most preferred embodiment the alkynyl group of the invention is ethynyl; 1-, or 2-propynyl; 1-, 2-, or 3-butynyl, or 1,3-butdiynyl; 1-, 2-, 3-, 4-pentynyl, or 1,3-pentdiynyl; 1-, 2-, 3-, 4-, or 5-henynyl, or 1,3-hexdiynyl or 1,3,5-hextriynyl; 1-, 2-, 3-, 4-, 5- or 6-heptynyl, or 1,3-heptdiynyl, or 1,3,5-hepttriynyl; 1-, 2-, 3-, 4-, 5-, 6- or 7-octynyl, or 1,3-octdiynyl, or 1,3,5-octtriynyl, or 1,3,5,7-octtetraynyl.

In the context of this invention a cyclic alkenyl group designates the cyclic form of an alkenyl group as defined above. Examples of preferred cyclic alkenyl groups of the invention include cyclopent-1-enyl; cyclopenta-1,3-dienyl; cyclohex-1-enyl; cyclohexa-1,3-dienyl; cyclohept-1-enyl; cyclohepta-1,3-dienyl; cyclooct-1-enyl; and cycloocta-1,3-dienyl.

In the context of this invention a cyclic alkynyl group designates the cyclic form of an alkynyl group as defined above. Examples of preferred cyclic alkynyl groups of the invention include cyclopent-1-ynyl; cyclopenta-1,3-diynyl; cyclohex-1-ynyl; cyclohexa-1,3-diynyl; cyclohept-1-ynyl; cyclohepta-1,3-diynyl; cyclooct-1-ynyl; and cycloocta-1,3-diynyl.

In the context of this invention an amino group may be a primary (—NH$_2$), secondary (—NH-alkyl), or tertiary (—N(alkyl)$_2$) amino group, i.e. it may be substituted once or twice with an alkyl group as defined above.

In the context of this invention an aromatic mono- or polycyclic carbocyclic group designates an aromatic hydrocarbon (aryl) group. Examples of preferred aryl groups of the invention include phenyl, indenyl, naphthyl, azulenyl, fluorenyl, and anthracenyl.

In the context of this invention an aryloxy group designates an "aryl-O—" group, wherein aryl is as defined above.

In the context of this invention an aralkyl group designates an aryl group as defined above, which aryl group is attached to an alkyl group as also defined above. Examples of preferred aralkyl groups of the invention include benzyl.

In the context of this invention an aromatic mono- or polycyclic heterocyclic group designates an aromatic heteroaryl group, which holds one or more heteroatoms in its ring structure. The term "bi- and poly-heterocyclic groups" includes benzo-fused five- and six-membered heterocyclic rings containing one or more heteroatoms. Preferred heteroatoms include nitrogen (N), oxygen (O), and sulphur (S).

Preferred monocyclic heteroaryl groups of the invention include aromatic 5- and 6 membered heterocyclic monocyclic groups, including furanyl, in particular 2- or 3-furanyl; thienyl, in particular 2 or 3-thienyl; selenophenyl, in particular 2- or 3-selenophenyl; pyrrolyl (azolyl), in particular 2 or 3-pyrrolyl; oxazolyl, in particular oxazol-2,4 or 5-yl; thiazolyl, in particular thiazol-2,4 or 5-yl; imidazolyl, in particular 2 or 4-imidazolyl; pyrazolyl, in particular 1,3 or 4-pyrazolyl; isoxazolyl, in particular isoxazol-3,4 or 5-yl; isothiazolyl, in particular isothiazol-3,4 or 5-yl; oxadiazolyl, in particular 1,2,3-oxadiazol-4 or 5-yl, or 1,3,4-oxadiazol-2-yl; triazolyl, in particular 1,2,3-triazol-4-yl or 1,2,4-triazol-3-yl; thiadiazolyl, in particular 1,2,3-thiadiazol-4 or 5-yl, or 1,3,4-thiadiazol-2-yl; pyridinyl, in particular 2, 3 or 4-pyridinyl; pyridazinyl, in particular 3 or 4-pyridazinyl; pyrimidinyl, in particular 2, 4 or 5-pyrimidinyl; pyrazinyl, in particular 2 or 3-pyrazinyl; and triazinyl, in particular 1,2,4- or 1,3,5-triazinyl.

Preferred bicyclic heteroaryl groups of the invention include indolizinyl, in particular 2,5 or 6-indolizinyl; indolyl, in particular 2,5 or 6-indolyl; isoindolyl, in particular 2,5 or 6-isoindolyl; benzo[b]furanyl, in particular 2,5 or 6-benzofuranyl; benzo[b]thienyl, in particular 2,5 or 6-benzothienyl; benzoimidazolyl, in particular 2,5 or 6-benzoimidazolyl; benzothiazolyl, in particular 5 or 6-benzothiazolyl; purinyl, in particular 2 or 8-purinyl; quinolinyl, in particular 2,3,6, or 7-quinolinyl; isoquinolinyl, in particular 3,6 or 7-isoquinolinyl; cinnolinyl, in particular 6 or 7-cinnolinyl; phthalazinyl, in particular 6 or 7-phthalazinyl; quinazolinyl, in particular 2,6 or 7-quinazolinyl; quinoxalinyl, in particular 2 or 6-quinoxalinyl; 1,8-naphthyridinyl, in particular 1,8-naphthyridin-2,3,6 or 7-yl; and pteridinyl, in particular 2,6 or 7-pteridinyl.

In the context of this invention an azacyclic group designates a mono-, bi- or poly-cyclic heterocyclic group, which holds a nitrogen atom as heteroatom. The azacyclic groups of the invention preferably are 4-12 membered mono-, bi- or polycyclic heterocyclic groups.

Preferred azacyclic groups of the invention include 4-7 membered monocyclic heterocyclic groups, in particular a 4-7 membered monocyclic heterocyclic group selected from the group consisting of Aza Ia, Aza IIa, Aza IIb, Aza IIc, Aza IIIa, Aza IIIb, and Aza IVa:

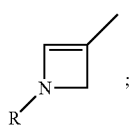

(Aza Ia)

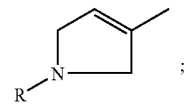

(Aza IIa)

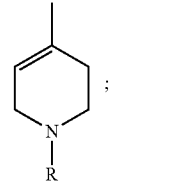

(Aza IIb)

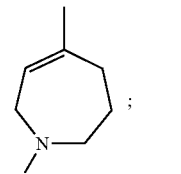

(Aza IIc)

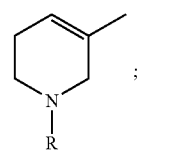

(Aza IIIa)

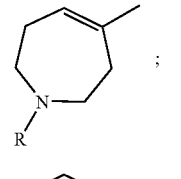

(Aza IIIb)

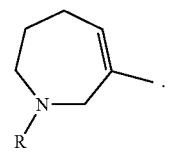

(Aza IVa)

Other preferred azacyclic groups of the invention include 9-10 membered bicyclic heterocyclic groups, in particular a 9-10 membered bicyclic group selected from the group consisting of Aza Va, Aza Vb, Aza Vc, Aza Via, Aza VIIa, Aza VIIIa:

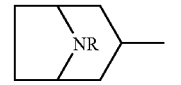

(Aza Va)

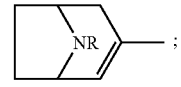

(Aza Vb)

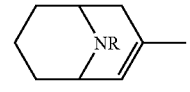

(Aza Vc)

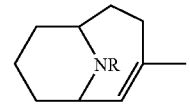

(Aza VIa)

-continued

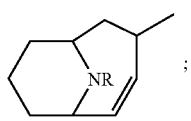 (Aza VIIa)

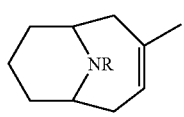 (Aza VIIIa)

Yet other preferred azacyclic groups of the invention include 8-10 membered tricyclic heterocyclic groups, in particular a 8-10 membered tricyclic heterocyclic group selected from the group consisting of Aza IXa, Aza IXb, Aza IXc and Aza IXd:

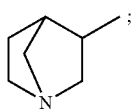 (Aza IXa)

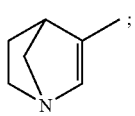 (Aza IXb)

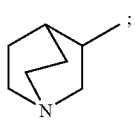 (Aza IXc)

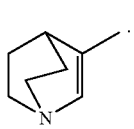 (Aza IXd)

Pharmaceutically Acceptable Salts

The azacyclic ethynyl derivative of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Metal salts of a chemical compound of the invention include alkali metal salts, such as the sodium salt of a chemical compound of the invention containing a carboxy group.

In the context of this invention the "onium salts" of N-containing compounds are also contemplated as pharmaceutically acceptable salts (aza-onium salts). Preferred aza-onium salts include the alkyl-onium salts, in particular the methyl- and the ethyl-onium salts; the cycloalkyl-onium salts, in particular the cyclopropyl-onium salts; and the cycloalkylalkyl-onium salts, in particular the cyclopropyl-methyl-onium salts.

Steric Isomers

The chemical compounds of the present invention may exist in (+) and (−) forms as well as in racemic forms. The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l-(tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials.

Methods of Producing Azacyclic Ethynyl Derivative

The azacyclic ethynyl derivatives of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The present invention relates to novel azacyclic ethynyl derivatives, which are found to be cholinergic ligands at the nicotinic acetylcholine receptors (nAChR), and modulators of the monoamine receptors, in particular the biogenic amine transporters such as the serotonin receptor (5-HTR), the dopamine receptor (DAR) and the norepinephrine receptor (NER), and of the biogenic amine transporters for serotonin (5-HT), dopamine (DA) and norepinephrine (NE). Also preferred azacyclic ethynyl derivatives of the invention show selective α7 activity. The compounds of the present invention may in particular be agonists, partial agonists, antagonists and allosteric modulators of the receptor.

Due to their pharmacological profile the compounds of the invention may be useful for the treatment of diseases or conditions as diverse as CNS related diseases, PNS related diseases, diseases related to smooth muscle contraction, endocrine disorders, diseases related to neuro-degeneration, diseases related to inflammation, pain, and withdrawal symptoms caused by the termination of abuse of chemical substances.

In a preferred embodiment the compounds of the invention are used for the treatment of diseases, disorders, or conditions relating to the central nervous system. Such diseases or disorders includes anxiety, cognitive disorders, learning deficit, memory deficits and dysfunction, Alzheimer's disease, attention deficit, attention deficit hyperactivity disorder (ADHD), Parkinson's disease, Huntington's disease, Amyotrophic Lateral Sclerosis, Gilles de la Tourette's syndrome, psychosis, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, periferic neuropathy, autism, dyslexia, tardive dyskinesia, hyperkinesia, epilepsy, bulimia, post-traumatic syndrome, social phobia, sleeping disorders, pseudodementia, Ganser's syndrome, pre-menstrual syndrome, late luteal phase syndrome, chronic fatigue syndrome, mutism, trichotillomania, and jet-lag.

In a preferred embodiment diseases, disorders, or conditions relating to the central nervous system for which the compounds of the invention are used are cognitive disorders, psychosis, schizophrenia and/or depression.

In another preferred embodiment the compounds of the invention may be useful for the treatment of diseases, disorders, or conditions associated with smooth muscle contractions, including convulsive disorders, angina pectoris, premature labour, convulsions, diarrhoea, asthma, epilepsy, tardive dyskinesia, hyperkinesia, premature ejaculation, and erectile difficulty.

In yet another preferred embodiment the compounds of the invention may be useful for the treatment of endocrine disorders, such as thyrotoxicosis, pheochromocytoma, hypertension and arrhythmias.

In still another preferred embodiment the compounds of the invention may be useful for the treatment of neurodegenerative disorders, including transient anoxia and induced neuro-degeneration.

In even another preferred embodiment the compounds of the invention may be useful for the treatment of inflammatory diseases, disorders, or conditions, including inflammatory skin disorders such as acne and rosacea, Chron's disease, inflammatory bowel disease, ulcerative colitis, and diarrhoea.

In still another preferred embodiment the compounds of the invention may be useful for the treatment of mild, moderate or even severe pain of acute, chronic or recurrent character, as well as pain caused by migraine, postoperative pain, and phantom limb pain. The pain may in particular be neuropathic pain, chronic headache, central pain, pain related to diabetic neuropathy, to post therapeutic neuralgia, or to peripheral nerve injury.

Finally the compounds of the invention may be useful for the treatment of withdrawal symptoms caused by termination of use of addictive substances. Such addictive substances include nicotine containing products such as tobacco, opioids such as heroin, cocaine and morphine, benzodiazepines and benzodiazepine-like drugs, and alcohol. Withdrawal from addictive substances is in general a traumatic experience characterised by anxiety and frustration, anger, anxiety, difficulties in concentrating, restlessness, decreased heart rate and increased appetite and weight gain.

In this context "treatment" covers treatment, prevention, prophylactics and alleviation of withdrawal symptoms and abstinence as well as treatment resulting in a voluntary diminished intake of the addictive substance.

In another aspect, the compounds of the invention are used as diagnostic agents, e.g. for the identification and localisation of nicotinic receptors in various tissues.

Neuroimaging

The azacyclic ethynyl derivatives of the invention may be useful as diagnostic tools or monitoring agents in various diagnostic methods, and in particular for in vivo receptor imaging (neuroimaging).

In another aspect of the invention, a method for the non-invasive determination of the distribution of a tracer compound inside a whole, intact living animal or human body using a physical detection method is provided. According to this method, a tracer compound is a compound of the invention, or any of its enantiomers or any mixture thereof, an N oxide thereof, a pharmaceutically acceptable salt thereof, in a labelled or un-labelled form.

In a preferred embodiment the physical detection method is selected from PET, SPECT; MRS, MRI, CAT, or combinations thereof.

The labelled compound of the invention preferably contains at least one radionuclide as a label. Positron emitting radionuclides are all candidates for usage. In the context of this invention the radionuclide is preferably selected from $^2$H (deuterium), $^3$H (tritium), $^{11}$C, $^{13}$C, $^{14}$C, $^{15}$O, $^{13}$N, $^{123}$I, $^{125}$I, $^{131}$I, $^{18}$F and $^{99m}$Tc.

An example of commercially available labelling agents, which can be used in the preparation of the labelled compounds of the present invention is $[^{11}C]O_2$, $^{18}$F, and NaI with different isotopes of Iodine.

In particular $[^{11}C]O_2$ may be converted to a $[^{11}C]$-methylating agent, such as $[^{11}C]H_3I$ or $[^{11}C]$-methyl triflate.

The tracer compound can be selected in accordance with the detection method chosen.

In one preferred embodiment, the labelled or unlabelled compound of the invention can be detected by a suitable spectroscopic method, in particular UV spectroscopy and/or fluorescence spectroscopy.

In anther preferred embodiment, the compounds of the invention labelled by incorporation of a isotope into the molecule, which may in particular be an isotope of the naturally occurring atoms including $^2$H (deuterium), $^3$H (tritium), $^{11}$C, $^{13}$C, $^{14}$C, $^{15}$O, $^{13}$N, $^{123}$I, $^{125}$I, $^{131}$I, $^{18}$F and $^{99m}$Tc, and the isotope incorporation may be measured by conventional scintillation counting techniques.

In a third preferred embodiment, the physical method for detecting said tracer compound of the present invention is selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Before conducting the method of the present invention, a diagnostically effective amount of a labelled or unlabelled compound of the invention is administered to a living body, including a human.

The azacyclic ethynyl derivative of the invention is believed to be particularly suited for in vivo receptor imaging (neuroimaging).

In a particularly preferred embodiment the physical method for detecting the azacyclic ethynyl derivative of the invention is Position Emission Tomography (PET).

It is currently believed that the diagnostically effective amount of the labelled or unlabelled compound of the invention, to be administered before conducting the in vivo method for the invention, is within a range of from 0.1 ng to 100 mg per kg body weight, preferably within a range of from 1 ng to 10 mg per kg body weight.

Pharmaceutical Compositions

In another aspect the invention provides novel pharmaceutical compositions comprising a therapeutically, effective amount of azacyclic ethynyl derivative of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the azacyclic ethynyl derivative of the invention, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in drags, in powder, or in liquid form, and parenteral administration, in particular cutaneous, subcutaneous, intramuscular, or intravenous injection. The pharmaceutical composition of the invention can be manufactured by any skilled person by use of standard methods and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

The azacyclic ethynyl derivatives of the present invention are valuable nicotinic and monoamine receptor modulators, and therefore useful for the treatment of a range of ailments involving cholinergic dysfunction as well as a range of disorders responsive to the action of nAChR modulators.

In another aspect the invention provides a method for the treatment, prevention or alleviation of a disease or a disorder or a condition of a living animal body, including a human, which disease, disorder or condition is responsive to modulation of cholinergic receptors and/or monoamine receptors, and which method comprises administering to such a living animal body, including a human, in need thereof an effective amount of an azacyclic ethynyl derivative of the invention.

The preferred indications for the method of the invention are those stated above.

In the context of this invention the term "treating" covers treatment, prevention, prophylaxis or alleviation, and the term "disease" covers illnesses, diseases, disorders and conditions related to the disease in question.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

A satisfactory result can, in certain instances, be obtained at a dosage as low as 0.005 mg/kg i.v. and 0.01 mg/kg p.o. The upper limit of the dosage range is about 10 mg/kg i.v. and 100 mg/kg p.o. Preferred ranges are from about 0.001 to about 1 mg/kg i.v. and from about 0.1 to about 10 mg/kg p.o.

EXAMPLES

The invention is further illustrated with reference to the following examples, which are not intended to be in any way limiting to the scope of the invention as claimed.

Example 1

(±)-8-Methyl-3-trifluoromethanesulfonyl-oxy-8-azabicyclo[3.2.1]oct-2-ene (Intermediate Compound)

To 8-methyl-8-azabicyclo[3.2.1]octan-3-one (12.65 g; 90.9 mmol) in tetrahydrofuran (300 ml), was added at −70° C.; sodium bis(trimethylsilyl)amide in tetrahydrofuran (77.5 ml; 77.5 mmol). The reaction mixture was stirred for 30 min at −70° C. N-phenylbis(trifluoromethane-sulfonamide) (32.5 g; 90.9 mmol) in tetrahydrofuran (200 ml) was added at −70° C. The reaction mixture was allowed to reach room temperature slowly and was stirred over night. Aqueous sodium hydroxide (0.1 M; 500 ml) was added and the mixture was extracted twice with ethyl acetate (200 ml). Chromatography on silica gel with dichloromethane and 10% ethanol as solvent gave the title compound as an oil. Yield 16.2 g, 45%.

(±)-8-Methyl-3-phenyletynyl-8-azabicyclo[3.2.1]oct-2-ene fumaric acid salt (Compound 1)

A mixture of (±)-8-Methyl-3-trifluoromethanesulfonyl-oxy-8-azabicyclo[3.2.1]-oct-2-ene (3.0 g; 11.0 mmol), lithium chloride (2.34 g; 55.3 mmol), phenylacetylene (2.26 g; 22.1 mmol), tetrakistriphenylphosphine palladium (0) (255 mg; 0.2 mmol), 1,3-propandiol (1.68 g; 22.1 mmol) and 1,2-dimethoxyethane. Aqueous sodium hydroxide (50 ml; 1 M) was added. The mixture was extracted with ethyl acetate (2×50 ml). Chromatography on silica gel with dichloromethane, methanol and conc. ammonia (89:10:1) gave the title compound as free base. Yield 0.14 g. (6%). The corresponding salt was obtained by addition of a diethyl ether and methanol mixture (9:1) saturated with fumaric acid. Mp 171-173° C.

Method A

(±)-3-Phenyletynyl-quinuclidin-2-ene (Compound A1)

To a mixture of phenylacetylene (23.2 g 227 mmol) and diethyl ether (250 ml) at −70° C., was added: butyllithium (100 ml, 250 mmol), followed by stirring at −70° C. for 30 min. 3-Quinuclidinone (28.4 g, 227 mmol), solved in tetrahydrofuran (250 ml) was added to the mixture at −70° C. followed by stirring 1 hour. The reaction was allowed to reach room temperature. Water (20 ml) was added followed by aqueous sodium hydroxide (200 ml, 1 M). The precipitated solid (±)3-phenyletynyl-quinuclidin-3-ol was filtered, yield 29.6 g (57%). Mp 167.5° C.

A mixture of 3-phenyletynyl-quinuclidin-3-ol (20.0 g, 88 mmol), thionylchloride (31.4 g, 263.9 mmol) and tetrahydrofuran (200 ml) was stirred at 50° C. for 30 min followed by evaporation. To the mixture was added: potassium-tert-butoxide (19.7 g, 176 mmol) and tert-butanol (200 ml), followed by reflux for 1.5 hour. The solvent was evaporated and aqueous sodium hydroxide (200 ml, 1 M) was added, and the mixture was extracted with ethyl acetate (3×125 ml). Chromatography on silica gel with dichloromethane, methanol and conc. ammonia (89:10:1) gave the title compound as free base. Yield 8.8 g (48%). The corresponding salt was obtained by addition of a diethyl ether and methanol mixture (9:1) saturated with fumaric acid. Mp 170.9° C.

(±)-8-Methyl-3-(2,4-difluorophenyletynyl)-8-azabicyclo[3.2.1]oct-2-ene fumaric acid salt (Compound A2)

Was prepared by method A using tropinone as starting-material. Mp. 164-167.5° C.

Method B

(±)-8,8-Dimethyl-3-phenyletynyl-8-azabicyclo[3.2.1]oct-2-ene iodide salt (Compound B1)

A mixture of (±)-8-methyl-3-phenyletynyl-8-azabicyclo[3.2.1]oct-2-ene (1.0 g, 4.5 mmol), methyl iodide (5.6 ml, 89.5 mmol) and dichloromethane (10 ml) was stirred for 15 hours. The reaction was evaporated and diethyl ether (30 ml) was added and the precipitate was filtered. Yield 1.27 g (77%). Mp 205.7° C.

(±)-1-Methyl-3-phenyletynyl-quinuclidin-2-ene iodide salt (Compound B2)

Was prepared from (±)-3-phenyletynyl-quinuclidin-2-ene by method B. Mp 204° C.

1-Methyl-3-phenyletynylpyridinium iodide (Intermediate Compound)

Was prepared according to method B from 3-phenyletynylpyridine.

2-Methyl-6-phenyl-hexa-3,5-diyn-2-ol (Intermediate Compound)

A mixture of bromophenylacetylene (5.0 g, 27.6 mmol), potassium carbonate (9.54 g, 69.0 mmol), copper iodide (0.54 g, 2.8 mmol), palladium on carbon (5%, 500 mg), triphenylphosphine (0.72 g, 2.8 mmol), 2-methyl-3-butyn-2-ol (11.6 g, 138 mmol) and 1,2-dimethoxyethane (100 ml) was stirred overnight at 100° C. The product mixture was evaporated. Chromatography on silica gel with petroleum and ethyl acetate (2:1), gave the title compound. Yield 1.06 g (21%).

Buta-1,3-diynylbenzene (Intermediate Compound)

A mixture of 2-methyl-6-phenyl-hexa-3,5-diyn-2-ol (3.8 g, 20.6 mmol) sodium hydride (60%, 83 mg, 2.06 mmol) and toluene (20 ml) was stirred at reflux for 1 hour. The mixture was evaporated. Chromatography on silica gel with petroleum and ethyl acetate (3:1), gave the title compound. Yield 0.54 g (21%).

(±)-8-Methyl-3-phenylbuta-1,3-diynyl-8-azabicyclo[3.2.1]oct-2-ene fumaric acid salt (Compound B3)

Was prepared according to method A and B from buta-1,3-diynylbenzene. Mp 195.4-211.9° C.

(±)-8-Methyl-3-(1-cyclohexenyletynyl)-8-azabicyclo[3.2.1]oct-2-ene fumaric acid salt (Compound B4)

Was prepared according to method A and B from 1-etynylcyclohexene. Mp 130.0-133.3° C.

(±)-3-(1-Cyclohexenyletynyl)-quinuclidine-2-ene Fumaric Acid Salt (Compound B5)

Was prepared according to method A and B from 1-etynylcyclohexene and quinuclidin-3-one. Mp 86.7-95.7° C.

(±)-8-Methyl-3-(3-phenylpropyn-1-yl)-8-azabicyclo[3.2.1]oct-2-ene fumaric acid salt (Compound B6)

Was prepared according to method A and B from phenyl-1-propyn. Hygroscopic salt.

(±)-8-Methyl-3-(4-toluyletynyl)-8-azabicyclo[3.2.1]oct-2-ene hydrochloric acid salt (Compound B7)

Was prepared according to method A and B from 4-etynyltoluene. Mp 250-251° C.

(±)-8-Methyl-3-(4-methoxyphenyletynyl)-8-azabicyclo[3.2.1]oct-2-ene hydrochloric acid salt (Compound B8)

Was prepared according to method A and B from etynyl-4-methoxybenzene. Mp 254-256° C.

(±)-8-Methyl-3-(2-methyl-but-1-en-3-ynyl)-8-azabicyclo[3.2.1]oct-2-ene hydrochloric acid salt (Compound B9)

Was prepared according to method A and B from 2-methyl-1-buten-3-yn. Mp 152.3-155.7° C.

Method C

(±)-8-H-3-Phenyletynyl-8-azabicyclo[3.2.1]oct-2-ene fumaric acid salt (Compound C1)

A mixture of (±)-8-Methyl-3-phenyletynyl-8-azabicyclo[3.2.1]oct-2-ene (1.0 g, 4.5 mmol) and xylene (15 ml) was stirred at reflux for 3 days. Methanol (15 ml) was added and the mixture was stirred at reflux for 3 days. The solvent was evaporated and aqueous sodium hydroxide (50 ml, 1 M) was added and the mixture was extracted with ethyl acetate (3×50 ml). Chromatography on silica gel with dichloromethane, methanol and conc. ammonia (89:10:1) gave the title compound as free base. The corresponding salt was obtained by addition of a diethyl ether and methanol mixture (9:1) saturated with fumaric acid. Mp 181.6° C. Yield 0.83 g (57%).

3-Phenyletynyl-1,2,5,6-tetrahydropyridine fumaric acid salt (Compound C2)

Was prepared according to method A, B and C from N-methyl-3-phenyletynyl-1,2,5,6-tetrahydropyridine. Mp 158-160° C.

N-Methyl-3-phenyletynyl-1,2,5,6-tetrahydropyridine fumaric acid salt (Compound C3)

A mixture of 1-methyl-3-phenyletynylpyridinium iodide (16.8 g, 52.3 mmol), sodiumborohydride (4.0 g, 104.6 mmol) and methanol (100 ml) was stirred at room temperature for 15 hours. The solvent was evaporated and aqueous sodium hydroxide (50 ml, 1 M) was added and the mixture was extracted with dichloromethane (3×50 ml). Chromatography on silica gel with dichloromethane, methanol and conc. ammonia (89:10:1) gave the title compound as free base. The corresponding salt was obtained by addition of a diethyl ether and methanol mixture (9:1) saturated with fumaric acid. Mp 185-190° C. Yield 2.17 g (21%).

Example 2

In Vitro Inhibition of $^3$H-α-Bungarotoxine Binding in Rat Brain

In this example the affinity of the compounds of the invention for binding to $\alpha_7$-subtype of nicotinic receptors is determined.

α-Bungarotoxine is a peptide isolated from the venom of the Elapidae snake *Bungarus multicinctus*. It has high affinity for neuronal and neuromuscular nicotinic receptors, where it acts as a potent antagonist.

$^3$H-α-Bungarotoxine labels nicotinic acetylcholine receptors formed by the $\alpha_7$ subunit isoform found in brain and the $\alpha_1$ isoform in the neuromuscular junction.

Tissue Preparation

Preparations are performed at 0-4° C. Cerebral cortices from male Wistar rats (150-250 g) are homogenised for 10 seconds in 15 ml of 20 mM Hepes buffer containing 118 mM NaCl, 4.8 mM KCl, 1.2 mM MgSO$_4$ and 2.5 mM CaCl$_2$ (pH 7.5) using an Ultra-Turrax homogeniser. The tissue suspension is subjected to centrifugation at 27,000×g for 10 minutes. The supernatant is discarded and the pellet is washed twice by centrifugation at 27,000×g for 10 minutes in 20 ml of fresh buffer, and the final pellet is then re-suspended in fresh buffer containing 0.01% BSA (35 ml per g of original tissue) and used for binding assays.

Assay

Aliquots of 500 μl of homogenate are added to 25 μl of test solution and 25 μl of $^3$H-α-bungarotoxine (2 nM, final concentration) and mixed and incubated for 2 hours at 37° C. Non-specific binding is determined using (−)-nicotine (1 mM, final concentration). After incubation, the samples are added 5 ml of ice-cold Hepes buffer containing 0.05% PEI and poured directly onto Whatman GF/C glass fibre filters (pre-soaked in 0.1% PEI for at least 6 hours) under suction, and immediately washed with 2×5 ml ice-cold buffer.

The amount of radioactivity on the filters is determined by conventional liquid scintillation counting. Specific binding is total binding minus non-specific binding.

The test value is given as an IC$_{50}$ (the concentration of the test substance which inhibits the specific binding of $^3$H-α-bungarotoxin by 50%).

The results of these experiments are presented in Table 1 below.

TABLE 1

| Inhibition of $^3$H-α-Bungarotoxine Binding | |
|---|---|
| Compound No. | IC$_{50}$ (μM) |
| 1 | 0.32 |
| B1 | 0.002 |
| A1 | 0.18 |
| B2 | 0.60 |

Example 3

In Vitro Inhibition of $^3$H-5-Hydroxytryptamine Uptake in Cortical Synaptosomes Serotonin transporters/uptake sites on nerve terminals presumably function to terminate neuronal signaling by removing serotonin from the synaptic cleft. The activity of the serotonin transporter integral protein can be measured in vitro by synaptosomal uptake of $^3$H-5-hydroxytryptamine (5-HT, serotonin).

Preparations are performed at 0-4° C. Cerebral cortices from male Wistar rats (150-200 g) are homogenized for 5-10 seconds in 100 volumes of ice-cold 0.32 M sucrose containing 1 mM pargyline, using a motor driven teflon pestle in a glass homogenizing vessel. Monoamine oxidase activity is inhibited in the presence of pargyline.

The homogenate is subjected to centrifugation at 1000×g for 10 minutes. The resulting supernatant is then centrifuged at 27,000×g for 50 minutes and the supernatant is discarded. The pellet (P$_2$) is re-suspended in oxygenated (equilibrated with an atmosphere of 96% O$_2$: 4% CO$_2$ for at least 30 minutes) Krebs-Ringer incubation buffer (1000 ml per g of original tissue) at pH 7.2 containing 122 mM NaCl, 0.16 mM EDTA, 4.8 mM KCl, 12.7 mM Na$_2$HPO$_4$, 3.0 mM NaH$_2$PO$_4$, 1.2 mM MgSO$_4$, 1 mM CaCl$_2$, 10 mM glucose and 1 mM ascorbic acid.

Aliquots of 4.0 ml tissue suspension are added to 100 μl of test solution and 100 μl of $^3$H-5-HT (1 nM, final concentration), mixed and incubated for 30 minutes at 37° C. Non-specific uptake is determined using Citalopram (1 μM, final concentration, available from Lundbeck, Denmark).

After incubation, the samples are poured directly onto Whatman GF/C glass fibre filters under suction. The filters are washed three times with 5 ml of ice-cold 0.9% (w/v) NaCl solution.

The amount of radioactivity on the filters is determined by conventional liquid scintillation counting. Specific uptake is calculated as the difference between total uptake and non-specific uptake.

25-75% inhibition of specific binding must be obtained, before calculation of an $IC_{50}$.

The test value is given as $IC_{50}$ (the concentration (μM) of the test substance which inhibits the specific binding of $^3$H-5-HT by 50%).

The results are presented in Table 2 below.

TABLE 2

Inhibition of $^3$H-5-Hydroxytryptamine Uptake

| Compound No. | $IC_{50}$ (μM) |
|---|---|
| 1 | 0.11 |
| C1 | 0.099 |
| A1 | 0.42 |
| B2 | 0.10 |

The invention claimed is:

1. An azacyclic ethynyl derivative of Formula II:

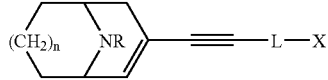

any of its enantiomers or any mixture of its enantiomers, or a pharmaceutically acceptable salt thereof, wherein n is 0;

R represents hydrogen, alkyl or cycloalkyl;

L is absent; and

X represents an aromatic mono- or polycyclic, carbocyclic group, which aromatic group is optionally substituted one or more times with alkyl, cycloalkyl, cycloalkylalkyl, alkoxy, cycloalkoxy, halogen, $CF_3$, $OCF_3$, cyano, amino, nitro, aryl, aryloxy and/or aralkyl.

2. The azacyclic ethynyl derivative of claim 1, wherein R represents hydrogen or alkyl; and X represents a phenyl group, which phenyl is optionally substituted one or two times with alkyl, cycloalkyl, alkoxy, cycloalkoxy, halogen, $CF_3$, $OCF_3$, cyano, amino, or nitro.

3. The azacyclic ethynyl derivative of claim 2, which is (±)-8-Methyl-3-phenyletynyl-8-azabicyclo[3.2.1]oct-2-ene;

(±)-8,8-Dimethyl-3-phenyletynyl-8-azabicyclo[3.2.1]oct-2-ene iodide;

(±)-8-H-3-Phenyletynyl-8-azabicyclo[3.2.1]oct-2-ene;

(±)-8-Methyl-3-(2,4-difluorophenyletynyl)-8-azabicyclo[3.2.1]oct-2-ene;

(±)-8-Methyl-3-(1-cyclohexenyletynyl)-8-azabicyclo[3.2.1]oct-2-ene;

(±)-8-Methyl-3-(4-toluyletynyl)-8-azabicyclo[3.2.1]oct-2-ene;

(±)-8-Methyl-3-(4-methoxyphenyletynyl)-8-azabicyclo[3.2.1]oct-2-ene; or or an enantiomer or a mixture of its enantiomers, or a pharmaceutically acceptable salt thereof.

4. A pharmaceutical composition comprising a therapeutically effective amount of an azacyclic ethynyl derivative of claim 1, or a pharmaceutically-acceptable addition salt thereof, together with at least one pharmaceutically-acceptable carrier or diluent.

* * * * *